United States Patent

Beck et al.

Patent Number: 4,548,936
Date of Patent: Oct. 22, 1985

[54] Δ¹-PYRROLINE THIOLACTIM ETHERS AND A PROCESS FOR THEIR PREPARATION

[75] Inventors: Gerhard Beck, Frankfurt am Main; Wilhelm Bartmann, Bad Soden am Taunus; Jochen Knolle, Kriftel; Richard H. Rupp, Königstein, all of Fed. Rep. of Germany

[73] Assignee: Hoechst Aktiengesellschaft, Frankfurt, Fed. Rep. of Germany

[21] Appl. No.: 375,106

[22] Filed: May 5, 1982

[30] Foreign Application Priority Data

May 7, 1981 [DE] Fed. Rep. of Germany ....... 3117979

[51] Int. Cl.⁴ ................. C07D 207/24; C07D 405/06; C07D 409/06; A61K 31/40
[52] U.S. Cl. .................... 514/422; 514/424; 548/517; 548/527; 548/551
[58] Field of Search ............ 548/517, 527, 551; 514/422–424

[56] References Cited

U.S. PATENT DOCUMENTS 4,371,542 2/1983 Beck et al. ................. 424/274

FOREIGN PATENT DOCUMENTS 2100422 7/1971 Fed. Rep. of Germany .
2452536 5/1976 Fed. Rep. of Germany ...... 548/551

OTHER PUBLICATIONS

Burger ed., *Medicinal Chemistry*, 2nd ed., Interscience Pub., (1960), p. 42.
Chem. Abstracts 97: 198060p (1982).
Tetrahedron Letters 23, 2947–2950, (1982).

*Primary Examiner*—Donald G. Daus
*Assistant Examiner*—William A. Teoli, Jr.
*Attorney, Agent, or Firm*—Curtis, Morris & Safford

[57] ABSTRACT

The present invention relates to Δ¹-pyrroline thiolactim ethers of the general formula I

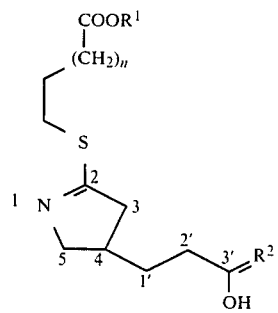

which have a more specific action and/or a longer-lasting action than PGI₂, and to a process for their preparation.

The compounds are distinguished by a platelet aggregation-inhibiting action and a blood vessel-relaxing and hypotensive action, and can therefore be used as medicaments.

4 Claims, No Drawings

$\Delta^1$-PYRROLINE THIOLACTIM ETHERS AND A PROCESS FOR THEIR PREPARATION

Prostacyclin PGI$_2$, a naturally occurring substance from the family of prostaglandins which was isolated in 1976, is distinguished by its highly pronounced platelet aggregation-inhibiting properties (The Lancet 1977, 18). Furthermore, PGI$_2$ is capable of relaxing some blood vessels, for example coronary arteries (Prostaglandins 13, 3, 1977), so that it can be used for the therapy and prophylaxis of thromboses and infarctions. PGI$_2$ also exhibits a marked hypotensive action (for example IRCS Med. Sci. 6, 392 (1978)).

The present invention relates to new compounds of the general formula I

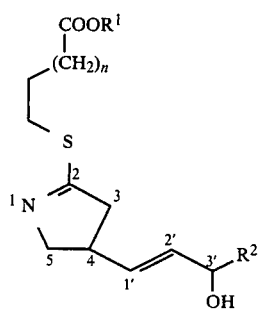

which have a more specific action and/or longer-lasting action than PGI$_2$, and in which R$^1$ denotes hydrogen, a straight-chain or branched alkyl radical with up to 8 carbon atoms, a straight-chain or branched unsaturated aliphatic hydrocarbon radical with 3 to 6 carbon atoms, a cycloaliphatic hydrocarbon radical with 3 to 7 carbon atoms, an araliphatic hydrocarbon radical with 7 to 9 carbon atoms or a physiologically acceptable metal ion, NH$_4$ ion or ammonium ion which is derived from a primary, secondary or tertiary amine, or a tetraalkylammonium ion, R$^2$ denotes an aryl radical, which can be mono-, di- or tri-substituted in the nucleus by halogen, trifluoromethyl and/or alkyl or alkoxy with in each case 1-6 C atoms, or denotes a cycloaliphatic radical with 3-8 carbon atoms, a straight-chain or branched alkyl radical with up to 8 carbon atoms or a straight-chain or branched unsaturated aliphatic hydrocarbon radical with 3 to 8 carbon atoms, it being possible for the aliphatic radicals in turn to be substituted by (a) a straight-chain or branched alkoxy radical with up to 6 carbon atoms, a straight-chain or branched alkenyloxy or alkynyloxy radical with 3 to 6 carbon atoms or an arylmethoxy radical, (b) halogen, cycloalkyl with 3-7 C atoms, phenyl or an $\alpha$- or $\beta$-thienyl or $\alpha$- or $\beta$-furyl radical, which can in turn be mono-, di- or tri-substituted in the nucleus by halogen, trifluoromethyl and/or alkyl or alkoxy with 1-6 C atoms, or (c) a phenoxy or $\alpha$- or $\beta$-thienyloxy radical or a cycloalkoxy radical with 3-7 carbon atoms, it being possible for the radicals mentioned to be in turn mono-, di- or tri-substituted in the nucleus by halogen, trifluoromethyl and/or alkyl or alkoxy with in each case 1-6 C atoms, and n denotes the number 0, 1, 2, 3 or 4.

Preferred substituents R$^1$ are: hydrogen, straight-chain or branched alkyl with up to 8 C atoms, straight-chain or branched unsaturated, aliphatic hydrocarbon radicals with up to 4 C atoms, cycloaliphatic hydrocarbon radicals with 5-7 C atoms, araliphatic hydrocarbon radicals with 8 or 9 C atoms and ammonium ions which are derived from primary, secondary or tertiary amines, and especially hydrogen, methyl, ethyl, n-butyl, n-pentyl, n-hexyl, n-heptyl, 2-propyl, 2-butyl, 2-pentyl, 3-hexyl, 2-methylpropyl, 2-methylbutyl, 4,4-dimethylpentyl, 5,5-dimethylhexyl, cyclopentyl, cyclohexyl, cycloheptyl, methylammonium, dicyclohexylammonium and tris-(hydroxymethyl)-methylammonium.

Particularly preferred substituents R$^2$ are the following: unsubstituted phenyl or phenyl which is mono-substituted by halogen, trifluoromethyl, C$_{1-4}$-alkyl or C$_{1-4}$-alkoxy, and straight-chain or branched C$_{3-7}$-alkyl, which can be substituted by optionally substituted C$_{5-7}$-cycloalkyl, by C$_{1-3}$-alkoxy, by phenoxy or halogenophenoxy, by thienyloxy or halogenothienyloxy, by cyclohexyloxy, by thienyl, by halogenothienyl or by furyl, and in particular the radicals n-pentyl, 1,1-dimethylpentyl, cyclopentylmethyl, cyclohexylmethyl, 1,1-dimethyl-2-ethoxyethyl, 1,1-dimethyl-2-methoxyethyl, 1,1-dimethyl-cyclohexyloxymethyl, 1-fluoropentyl, 1-chloropentyl, 5-fluoropentyl, 5-chloropentyl, 3-thienyl-2-ethyl, 2-thienyl-2-ethyl, 3-(2-chlorothienyl)-2-ethyl, 2-(5-chlorothienyl)-2-ethyl, phenoxymethyl, 3-chlorophenoxymethyl, 2-thienyloxymethyl, 3-(2-chlorothienyl)-oxymethyl, 2-(5-chlorothienyl)-oxymethyl, 3-furyl-2-ethyl, 2-furyl-2-ethyl, 2,2,3,3-tetrafluorocyclobutyl-2-ethyl, phenyl, 3-chlorophenyl and 3-trifluoromethylphenyl.

n preferably denotes 0, 1 or 2.

The invention also relates to a process for the preparation of the compounds of the formula I, which comprises (a) converting the lactam of the formula II

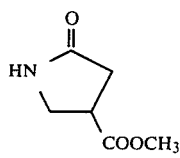

into the thiolactam of the formula III

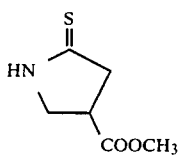

by conventional methods, (b) converting the thiolactam of the formula III into the thiolactam alcohol IV

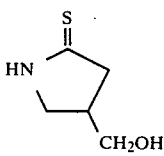

by reduction of the ester group, (c) alkylating the thiolactam alcohol of the formula IV with a compound of the formula V

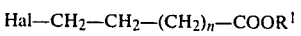

in which R¹ and n have the meaning given in the case of formula I and Hal denotes iodine, chlorine or bromine, to give a compound of the formula VI

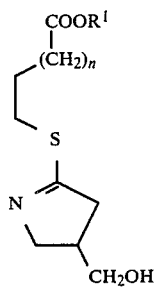

VI (d) oxidizing the compound of the formula VI to an aldehyde of the formula VII

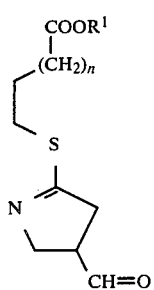

VII in which R¹ and n have the meaning given above, (e) reacting the aldehyde of the formula VII with a phosphonate of the formula VIII

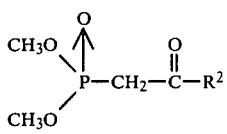

VIII in which R² has the meaning given in the case of formula I, to give an enone of the formula IX

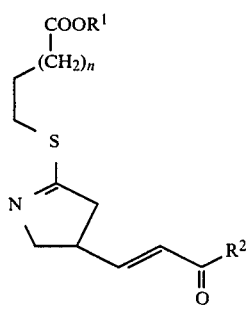

IX in which R¹, R² and n have the meaning given in the case of formula I, (f) reducing the enone of the formula IX with a reducing agent in a known manner to give an epimer mixture of the alcohols of the formula I in which R¹, R² and n have the meaning given in the case of formula I, (g) where appropriate, hydrolyzing a compound of the formula I in which R¹ is not hydrogen or a cation to give a compound of the formula I in which R¹ is hydrogen or a physiologically acceptable cation, and (h) where appropriate, replacing the cation R¹ in a compound of the formula I in which R¹ is hydrogen or a physiologically acceptable metal ion, NH₄ ion or ammonium ion which is derived from a primary, secondary or tertiary amine and R² and n have the meanings given in the case of formula I, by another cation.

The lactam II used as the starting material in the process according to the invention can be prepared by a process analogous to that described by P. L. Paytash, E. Sparrow and I. C. Gathe, J. Am. Chem. Soc. 72, 1415 (1950).

The thiolactam of the formula III can be prepared from the lactam of the formula II by reaction with reagents which transfer sulfur, such as, for example, phosphorus pentasulfide, phosphorus pentasulfide/calcium oxide, a phosphorus pentasulfide-pyridine complex or a phosphorus pentasulfide-anisole complex, in inert solvents, such as, for example, toluene, dimethoxyethane or pyridine, by methods which are known from the literature (cf., for example, Bull. Soc. Chim. Belg. 87, (3), 229 (1978)). The thiolactam alcohol of the formula IV is obtained if the thiolactam of the formula III is reacted with a complex metal hydride, preferably an alkali metal boranate, such as sodium, potassium or lithium borohydride. To prepare thiolactim ethers of the formula VI, the thiolactam of the formula IV is alkylated with alkyl halides of the formula V. This reaction is carried out in an inert solvent, such as, for example, toluene, tetrahydrofuran, dimethoxyethane or dimethylformamide, in the presence of a base, such as, for example, pyridine, triethylamine, potassium carbonate or sodium hydride, at 15°–180° C. A preferred embodiment of this reaction comprises preparing the S-potassium salt of the thiolactam of the formula IV with potassium carbonate in dimethylformamide, adding dropwise a solution of the compound of the formula V in dimethylformamide and stirring the mixture at 90°–160° C. for 1–6 hours. An alcohol of the formula VI can be oxidized to an aldehyde of the formula VII by oxidizing agents such as pyridinium chlorochromate, in inert solvents, such as methylene chloride or chloroform. A further oxidation possibility comprises reaction with thioanisole/Cl₂/trimethylamine in carbon tetrachloride. The aldehyde of the formula VII is advantageously subsequently processed without further purification.

An aldehyde of the formula VII is then reacted with a phosphoric acid ester of the formula VIII by the Horner-Emmons-Wittig reaction to give an unsaturated ketone of the formula IX, a preferred embodiment comprising preparing the sodium salt of the phosphonic acid ester of the formula VIII with sodium hydride in dimethoxyethane, subsequently adding the aldehyde of the formula VII and then allowing the reaction to proceed at room temperature for 2–6 hours. The phosphonic acid esters of the formula VIII can be prepared by processes which are known from the literature (cf., for example, J. Am. Chem. Soc. 88, 5654 (1966)).

The compounds of the formula I are obtained in the form of their epimer mixtures by reducing an enone of the formula IX with a complex metal hydride, preferably with an alkali metal boranate, or with D,L-isobornyloxyaluminum isopropoxide.

Compounds of the formula I in which R¹ does not represent hydrogen or a cation can be hydrolyzed to compounds of the formula I in which R¹ denotes hydrogen or a cation in a conventional manner in an alkaline medium, for example using NaOH or KOH in a low-molecular alcohol, such as methanol, or an ether, such as dimethoxyethane or tetrahydrofuran, where appropriate in the presence of water. An equimolar amount or a very slight excess of alkali metal hydroxide is advantageously used, so that the alkali metal salt of the formula I ($R^1$ = alkali metal ion) is obtained by evaporating off the solvent, preferably by freeze-drying.

The alkali metal cation can be replaced by any desired cations on ion exchangers in a conventional manner. For this replacement, a solution of the alkali metal salt of an imino-hetero-prostacyclin derivative according to the invention is allowed to run through a column packed with a cation exchanger, such as, for example, Amberlite CG-50 or Dowex CCR-2. The cation exchanger is loaded with the desired cation, for example with an ammonium ion which is derived from a primary, second or tertiary amine. The desired salt is obtained by evaporating the eluate.

Compounds of the formula I in which $R^1$ denotes $NH_4$ or an ammonium ion which is derived from a primary, secondary or tertiary amine can also be prepared by adding an equimolar amount of the corresponding amine to compounds of the formula I, in which $R^1$ denotes hydrogen, in alcoholic solution, and evaporating off the solvent.

Compounds of the formula I in which $R^1$ denotes hydrogen or a cation can be esterified to compounds of the formula I in which $R^1$ has the other meanings given in the case of formula I. Thus, for example, compounds of the formula I in which $R^1$ is H can be esterified with a diazoalkane of the formula $R^1 = N_2$ in which $R^1$ is alkyl at temperatures between $-40°$ and $+20°$ C., it being possible to use the conventional solvents, such as, for example, diethyl ether, tetrahydrofuran, chloroform or low-molecular alcohols, such as methanol. The resulting esters can be isolated in a simple manner by evaporating off the solvent, and if necessary can be purified by chromatography. One esterification method comprises reacting salts of the compounds of the formula I ($R^1$ = a cation) with an alkylating agent $R^1$—Z in the presence of a base, such as, for example, a metal alcoholate or metal carbonate, in a suitable solvent. Examples of possible metal alcoholates are sodium methylate, sodium ethylate and potassium tert.butylate, and an example of a suitable carbonate is calcium carbonate. Suitable solvents which can be used are alcohols, such as, for example, methanol or tert.butanol, ethers, such as tetrahydrofuran or 1,2-dimethoxyethane, and, in particular, dipolar aprotic solvents, such as dimethylformamide, dimethylsulfoxide, acetonitrile or N-methylpyrrolidone. In the formula $R^1$—Z, Z preferably denotes bromine or iodine or a sulfonic acid radical. The method of trans-esterification with an excess of alcohols, such as, for example, methanol, ethanol or isopropanol, is also suitable for the preparation of esters of the formula I ($R^1$ = alkyl).

The compounds of the formula I are obtained as a racemate in respect of the configuration at carbon atom 4 of the pyrroline ring, and as $\alpha/\beta$-isomers in respect of the carbon atom 3'. The $\alpha/\beta$-isomers are separated at the stage of the end products of the formula I. The racemic mixture in respect of the carbon atom 4 of the $\Delta$1-pyrroline ring can be separated into its components after each reaction stage, or the optically active (+) or (−) lactam II is employed. This means that all the reactions described can be carried out with epimer mixtures, pure epimers or optically active antipodes. The compounds of the formula I claimed thus include diastereomer mixtures, pure diastereomers, epimer mixtures and pure epimers.

If the respective reaction products are not already obtained in a sufficiently pure form for them to be used for the subsequent reaction step, purification by means of, for example, column, thin layer or high pressure liquid chromatography is advisable.

In addition to the compounds described in the examples, the following compounds can be prepared by the processes according to the invention: 2-(1-thia-5-carboxypentyl)-4-(3-hydroxy-1-octenyl)-$\Delta^1$-pyrroline, 2-(1-thia-4-carboxybutyl)-4-(3-hydroxy-1-octenyl)-$\Delta^1$-pyrroline, 2-(1-thia-6-carboxyhexyl)-4-(3-hydroxy-1-octenyl)-$\Delta^1$-pyrroline, 2-(1-thia-4-methoxycarbonylbutyl)-4-(3-hydroxy-1-octenyl)-$\Delta^1$-pyrroline, 2-(1-thia-5-methoxycarbonylpentyl)-4-(3-hydroxy-1-octenyl)-$\Delta^1$-pyrroline, 2-(1-thia-4-methoxycarbonylbutyl)-4-(3-hydroxy-5-(2-furyl)-1-pentenyl)-$\Delta^1$-pyrroline, 2-(1-thia-4-methoxycarbonylbutyl)-4-(3-hydroxy-4,4-dimethyl-4-cyclohexyloxy-1-butenyl)-$\Delta^1$-pyrroline, 2-(1-thia-4-methoxycarbonylbutyl)-(3-hydroxy-3-phenyl-1-propenyl)-$\Delta^1$-pyrroline, 2-(1-thia-4-ethoxycarbonylbutyl)-4-(3-hydroxy-4-(3-trifluoromethylphenoxy)-1-butenyl)-$\Delta^1$-pyrroline, 2-(1-thia-4-cyclohexyloxycarbonylbutyl)-4-(3-hydroxy-1-octenyl)-$\Delta^1$-pyrroline, 2-(1-thia-7-methoxycarbonylheptyl)-4-(3-hydroxy-1-octenyl-$\Delta^1$-pyrroline, 2-(1-thia-4-ethoxycarbonylbutyl)-4-(3-hydroxy-1-nonenyl)-$\Delta^1$-pyrroline and 2-(1-thia-4-methoxycarbonylbutyl-4-(3-hydroxy-1-decenyl)-$\Delta^1$-pyrroline.

The compounds of the formula I are distinguished by an inhibitory action on platelet aggregation, relaxation of the vascular walls and hypotensive properties. They can therefore be used as medicaments. The compounds of the formula I are used as hypotensive agents in the daily dose range from 0.01 mg/kg to 0.5 mg/kg, preferably from 0.05 mg/kg to 0.1 mg/kg, in the case of intravenous administration, or in the daily dose range from 0.05 mg/kg to 2 mg/kg, preferably from 0.1 to 1 mg/kg, in the case of oral administration. The same daily doses as given above, and in some cases even lower dosages, can be used for relaxation of the vascular walls, especially of the coronary arteries, and for inhibition of platelet aggregation.

The compounds can also be used on mammals, including humans, and on certain useful animals, for example dogs and pigs, for reducing and controlling excessive secretion of gastric juices, whereupon the formation of gastrointestinal ulcers can be reduced or avoided and the healing of such already existing ulcers can be accelerated. For this purpose, the compounds are injected or infused intravenously, subcutaneously or intramuscularly. In this treatment, the dosage plan for the prostaglandin depends on various factors, including the type, age, weight, sex and medical condition of the patient, the dosage plan of the antiphlogistic synthetase inhibitor and the sensitivity of the patient to the synthetase inhibitor in respect of its effect on the gastrointestinal tract. Thus, for example, not all patients who require an antiphlogistic substance experience the same unpleasant gastrointestinal effects. Rather, these frequently differ in nature and extent. It is thus within the doctor's or veterinary surgeon's field of experience to determine whether administration of the antiphlogistic substance produces undesirable gastrointestinal effects in humans or animals and to prescribe the active amount of the prostaglandin with which these effects can largely be eliminated. Some representatives of these substances are suitable for the treatment of asthma. They can be used, for example, as bronchidilators or as inhibitors of mediators, such as, for example, SRS-A and histamine, which are released from cells activated by an antigent/antibody complex. The compounds therefore combat spasms and facilitate breathing in illness conditions such as bronchitis, pneumonia and emphysema. For these purposes, the compounds are administered in various dosage forms, for example orally in the form of tablets, capsules or liquids, rectally in the form of suppositories, and parenterally, subcutaneously or intramuscularly, intravenous administration being preferred in emergency situations.

The compounds of the formula I according to the invention can be used as free acids, in the form of their physiologically acceptable inorganic or organic salts, or as esters. The acids and salts or esters can be administered in the form of their aqueous solutions or suspensions or as solutions or suspensions in pharmacologically acceptable organic solvents, such as monohydric or polyhydric alcohols, such as, for example, ethanol, ethylene glycol or glycerol, oils, such as, for example, sunflower oil or cod-liver oil, ethers, such as, for example, diethylene glycol dimethyl ether, or polyethers, such as, for example, polyethylene glycol, or in the presence of other pharmacologically acceptable polymeric excipients, such as, for example, polyvinylpyrrolidone.

Possible formulations are the conventional galenic infusion or injection solutions and tablets, as well as locally applicable formulations such as creams, emulsions, suppositories or aerosols.

The compounds of the formulae VI, VII and IX are new, valuable intermediate products for the preparation of compounds of the formula I.

EXAMPLE 1

4-Methoxycarbonyl-pyrrolidine-2-thione III 10 g of 4-methoxycarbonyl-pyrrolidine-2-one II (prepared as described in P. L. Paytash, E. Sparrow and I. C. Gathe, J. Am. Chem. Soc. 72, 1415 (1950)) were dissolved in 170 ml of absolute toluene under the influence of heat. 16.7 g of $P_4S_{10} \times 4$ pyridine (Riedel de Haen, Hanover, West Germany) and 42 g of kieselguhr (as a filtration aid) were then added in succession. The mixture was subsequently warmed at 90°–100° C. for 3 hours, while stirring and under nitrogen as an inert gas. The solid was then filtered off with suction and the residue on the filter was rinsed with hot toluene. The filtrate was concentrated in vacuo.

Yield: 7.64 g of light yellow crystals of melting point 106°–109° C. (70% of theory). $C_6H_9NSO_2$ MW=159.

NMR (CDCl$_3$): δ ppm=3.2 (s, 3H) COOCH$_3$; 3.1–4.1 (m, 5H) HN—CH$_2$, —CH$_2$CS and =CH—COOCH$_3$; and 8.3 (broad s, 1H) CSNH.

R$_f$ value: cyclohexane/acetone ½: 0.80.

EXAMPLE 2

4-Hydroxymethyl-pyrrolidine-2-thione IV 24.1 g of 4-methoxycarbonyl-pyrrolidine-2-thione III were dissolved in 250 ml of methanol. A solution of 12 g of sodium borohydride in 20 ml of ice-water was carefully added dropwise to this solution at 0°–10° C., while stirring. The mixture was then stirred at 10° C. for 2 hours and at room temperature for 1 hour. It was then acidified to pH 1–2 with half-concentrated hydrochloric acid, while cooling with ice. The sodium chloride precipitated was filtered off with suction over kieselguhr and washed with a little cold methanol and the filtrate was concentrated in vacuo. The residue was taken up with ethyl acetate+5% of methanol and the mixture was cooled and filtered with suction again. The filtrate was concentrated, a little acetone was added to the residue and the mixture was stored overnight in a refrigerator. The crystals which had precipitated were filtered off with suction at 0° C.

Yield: 15.4 (78% of theory) of white crystals of melting point 108°–111° C. $C_5H_9NSO$ MW=131.

NMR (CDCl$_3$): δ ppm=3.5–3.8 (m, 2H) CH$_2$OH and CSNH—CH$_2$; 1.6 (broad s, 1H) OH; 2.6–3.0 (m, 3H)

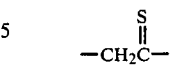

and >CH—CH$_2$OH; and 7.7 (broad s, 1H) —CSNH—.

R$_f$ value: cyclohexane/acetone 1/1: 0.28.

EXAMPLE 3

2-(1-Thia-5-ethoxycarbonyl-pentyl)-4-hydroxy-methyl-Δ$^1$-pyrroline VI (n=2)

5.1 g of 4-hydroxymethyl-pyrrolidine-2-thione IV in 15 ml of absolute dimethylformamide were added dropwise to 2.7 g of pulverulent potassium carbonate in 10 ml of absolute dimethylformamide, while stirring. The mixture was then stirred under nitrogen for 30 minutes and heated to 100° C. and 8.2 g of ethyl ω-bromovalerate in 6 ml of absolute dimethylformamide were added dropwise. After 2½ hours at 100° C., the reaction had ended.

The solvent (dimethylformamide) was removed in vacuo, the residue was taken up in ethyl acetate and H$_2$O, the mixture was neutralized with 2N hydrochloric acid and the aqueous phase was separated off. The ethyl acetate phase was washed again several times with water/saturated NaCl solution. The combined ethyl acetate phases were dried and concentrated in vacuo.

Yield: 14.3 g of a brownish oil, which was chromatographed over a Merck pre-packed column, size C (particle size of SiO$_2$: 0.063–0.2 mm) using the mobile phase cyclohexane/acetone=2:1. Fraction 240–370 gave 5.5 g (55% of theory) of VI. $C_{12}H_{21}NSO_3$ MW=259.

NMR (CDCl$_3$): δ ppm=1.2 (t, 3H) CO$_2$CH$_2$CN$_3$; 1.5–2.0 (m, 4H) —CH$_2$—CH$_2$—; 2.1–2.5 (m, 2H) CH$_2$—COOCH$_5$; 2.4–2.7 (m, 2H) CH$_2$—C=H; 2.95 (t, 2H) —S—CH$_2$—; 3.5 (d, 2H) CH$_2$OH 3.5–3.6 (m, 2H) N—CH$_2$; and 4.05 (q, 2H) CO$_2$CH$_2$CH$_3$.

R$_f$ value: cyclohexane/acetone 2/1:0.34.

EXAMPLE 4

2-(1-Thia-5-ethoxycarbonyl-pentyl)-Δ$^1$-pyrroline-4-aldehyde VII (n=2)

A solution of 1.63 g of absolute dimethylsulfoxide [20.9 mmoles, 1.48 ml] in 25 ml of absolute CH$_2$Cl$_2$ was cooled to −60° C. under a stream of N$_2$. 1.2 g of oxalyl chloride (9.6 mmoles, 0.84 ml) were added dropwise and stirring was continued for 10 minutes. A solution of 2.25 g of 2-(1-thia-5-ethoxycarbonyl-pentyl)-4-hydroxymethyl-Δ$^1$-pyrroline VI in 15 ml of absolute CH$_2$Cl$_2$ was then added dropwise and stirring was continued for 20 minutes at −60° C. 4.4 g of triethylamine (43.5 mmoles, 6.06 ml) were added dropwise at this temperature, and the solution was subsequently stirred for a further 30 minutes. It was then neutralized at −10° C.

to +20° C. by addition of ethanolic HCl. After the solution had been concentrated, the residue was taken up in ethyl acetate, the ammonium salt precipitated was filtered off and washed thoroughly with ethyl acetate and the filtrate was concentrated again.

Yield: 2.0 g (90% of theory) of VII as a light yellow oil. $C_{12}H_{19}NSO_3$ MW=257.

Rf value: cyclohexane/acetone 2/1:0.38.

MS: 257 (molecular mass).

NMR (CDCl$_3$): δ ppm=9.9 (d; 1H) >CH—C$\underline{H}$O.

EXAMPLE 5

2-(1-Thia-5-ethoxycarbonyl-pentyl)-4-(3-oxo-1-octenyl)-Δ$^1$-pyrroline IX (n=2)

0.35 g of 55% strength NaH was suspended in 20 ml of absolute dimethoxyethane under a stream of N$_2$ and the suspension was stirred at room temperature for 15 minutes. 1.64 g of dimethyl 2-oxoheptyl-phosphonate in 20 ml of absolute dimethoxyethane were added dropwise at room temperature (the white Na salt precipitated). The mixture was subsequently stirred for about 1 hour at a maximum temperature of 30° C. 2.0 g of 2-(1-thia-5-ethoxycarbonylpentyl)-Δ$^1$-pyrroline-4-aldehyde VII in 20 ml of dimethoxyethane were then added rapidly. The mixture was stirred at room temperature for about 2 hours.

When the reaction had ended, the mixture was acidified with glacial acetic acid (pH 5) and concentrated. The residue was taken up in ethyl acetate and washed with H$_2$O and saturated NaCl. The ethyl acetate phase was dried and concentrated.

Yield: 1.92 g (73.6% of theory) of IX as a light yellow oil. $C_{19}H_{31}O_3NS$ MW: 353.

MS: 353 (molecular mass).

NMR (CDCl$_3$): δ ppm=1.2 (t, 3H) CO$_2$CH$_2$C$\underline{H_3}$; 1.5–1.9 (m, 2H) CH$_2$—CH$_2$; 2.1–2.9 (m, 7H) C$\underline{H_2}$CO, =CH—, —CH$_2$—C=, and CH$_2$—CO$_2$CH$_2$CH$_3$; 3.0 (t, 2H) —S—C$\underline{H_2}$; 3.5–3.65 (m, 2H) N—CH$_2$; 4.05 (q, 2H) CO$_2$C$\underline{H_2}$CH$_3$ and 5.9–6.9 (ABX system, 2H) —HC=CH—.

Rf value: cyclohexane/acetone 2/1=0.57.

EXAMPLE 6

2-(1-Thia-5-ethoxycarbonyl-pentyl)-4-(3-hydroxy-1-octenyl)-Δ$^1$-pyrroline I (n=2)

17 ml of a 0.45 molar solution of bis-isobornyloxyisopropyloxy-aluminate were slowly added dropwise, under a stream of N$_2$, to 1.0 g of 2-(thia-5-ethoxycarbonylpentyl-4-(3-oxo-1-octenyl)-Δ$^1$-pyrroline IX, from Example 5, dissolved in 15 ml of absolute toluene. The mixture was stirred at room temperature and was worked up after 2 hours. Ethyl acetate was added to the reaction product, the mixture was extracted 3 times with saturated sodium hydrogen tartrate solution and the sodium hydrogen tartrate phase was washed again with ethyl acetate. The combined ethyl acetate phases were dried and concentrated.

Crude yield: 2.87 g of I as a light yellow oil, which was chromatographed over a Merck pre-packed column, size C/silica gel (particle size: 0.063–0.2 mm) using the mobile phase cyclohexane/ethyl acetate 1/1: fractions25–44=450 mg (3′β-epimer), fractions54–125=440 mg (3′α-epimer).

Yield: 0.9 g (90% of theory) of a light-colored oil $C_{19}H_{33}NSO_2$ MW=355.

MS: 355 (molecular mass).

NMR (CDCl$_3$): δ ppm spectra for the α- and β-epimers were identical within the usual resolution for 60 MHz—$^1$H. Signals as for Example 5, and additional signals at: 3.8–4.1 (m, 1H) C$\underline{H}$—OH, 5.45–5.6 (m, 3H) —CH=CH— (ABX system from Example 5 at 5.9–6.9 missing!)

Rf value: cyclohexane/ethyl acetate 1/1=0.39 (3′β-epimer) and 0.26 (3′α-epimer).

EXAMPLE 7

2-(1-Thia-4-ethoxycarbonyl-butyl)-4-hydroxy-methyl-Δ$^1$-pyrroline VI (n=1)

59.5 g of 4-hydroxymethyl-pyrrolidine-2-thione IV (Example 2), dissolved in 200 ml of absolute dimethylformamide, were added dropwise to 31.5 g (0.23 mole) of K$_2$CO$_3$ in 100 ml of absolute dimethylformamide. The mixture was then stirred at room temperature for 30 minutes (stream of N$_2$) and subsequently heated to 100° C., and 87.7 g (0.45 mole) of ethyl bromobutyrate, dissolved in 65 ml of dimethylformamide, were added dropwise. After 2½ hours at 100° C., the reaction had ended (thin layer chromatogram in cyclohexane/acetone 2/1, stained with iodine). The dimethylformamide was then stripped off at 80° C., the residue was taken up in ethyl acetate and H$_2$O and the mixture was neutralized with 2N HCl. The H$_2$O phase was separated off and the ethyl acetate phase was washed again several times with H$_2$O and saturated NaCl. The combined ethyl acetate phases were dried and concentrated. The residue was chromatographed over Merck silica gel (0.063–0.2 mm) using the mobile phase cyclohexane/acetone 3/1 (later cyclohexane/acetone 2/1).

Yield: 71 g (64% of theory) of a yellow oil. $C_{11}H_{19}NSO_3$ MW=245.

NMR (CDCl$_3$): δ ppm=1.2 (t, 3H) CO$_2$CH$_2$C$\underline{H_3}$; 1.8–2.1 (m, 2H)—CH$_2$—; 2.2–2.8 (m, 5H) CH—C$\underline{H_2}$OH, CH$_2$—COOC$_2$H$_5$ and =C—CH$_2$; 3.0 (t, 2H) —S—C$\underline{H_2}$—; 3.5 (d, 2H) C$\underline{H_2}$OH; 3.5–3.7 (m, 2H) N—CH$_2$; and 4.05 (q,2H) COO$\underline{C}$H$_2$;

Rf value: cyclohexane/acetone 2/1=0.31.

EXAMPLE 8

2-(Thia-4-ethoxycarbonyl-butyl)-Δ$^1$-pyrroline-4-aldehyde VII (n=1)

A fresh solution of 3.0 g of absolute dimethylsulfoxide (39.2 mmoles; 2.7 ml) in 35 ml of absolute CH$_2$Cl$_2$ was cooled to −60° C. under a stream of N$_2$. 2.25 g of oxalyl chloride (18 mmoles; 1.57 ml) were added dropwise and stirring was continued for 10 minutes. A solution of 4 g of 2-(1-thia-5-ethoxycarbonyl-butyl)-4-hydroxymethyl-Δ$^1$-pyrroline VI (Example 7) in 20 ml of CH$_2$Cl$_2$ was then added dropwise, and stirring was continued for 20 minutes at −60° C. 8.2 g of triethylamine (81.5 mmoles, 11.3 ml) were added dropwise at this temperature, and the solution was subsequently stirred for a further 30 minutes. The solution was then rendered neutral at 10° C. to +20° C. with ethanolic HCl. After the solution had been concentrated, the residue was taken up in ethyl acetate, the ammonium chloride precipitated was filtered off and washed thoroughly with ethyl acetate and the filtrate was concentrated again.

Yield: 3.5 g (88% of theory) of VII as a light yellow oil. $C_{11}H_{17}NSO_3$ MW=243.

Rf value: cyclohexane/acetone 2/1=0.34.

MS: 243 (molecular mass).

NMR (CDCl$_3$): δ ppm=9.8 (d; 1H) >CH—C$\underline{H}$O.

EXAMPLE 9a 2-(1-Thia-4-ethoxycarbonyl-butyl)-4-(3-oxo-1-octenyl)-$\Delta^1$-pyrroline IX (n=1)

1.05 g of 55% strength NaH were suspended in 30 ml of absolute dimethoxyethane and the suspension was stirred for 15 minutes. 4.92 g of dimethyl 2-oxoheptylphosphonate (22.2 mmoles) dissolved in 50 ml of absolute dimethoxyethane were added dropwise at room temperature (the white Na salt precipitated). The mixture was subsequently stirred for 1 hour at a maximum temperature of 30° C. 5.4 g of 2-(1-thia-4-ethoxycarbonyl-butyl)-$\Delta^1$-pyrroline-4-aldehyde VII (Example 8), dissolved in 30 ml of absolute dimethoxyethane were then added rapidly. After about 3 hours, the reaction had ended (thin layer chromatogram in cyclohexane/acetone 2/1). The mixture was acidified with acetic acid (pH 5), the reaction product was concentrated and taken up in ethyl acetate and the mixture was extracted 3 times with saturated NaCl. The ethyl acetate phase was dried and concentrated and the residue was chromatographed over a Merck silica gel column (particle size: 0.04–0.063 mm) using the mobile phase cyclohexane/acetone 5/1.

Yield: fractions 53–73 = 5.2 g (70% of theory) of IX as a light-colored oil. $C_{18}H_{29}O_3NS$ MW: 339.

MS: 339 (molecular mass).

NMR (CDCl$_3$): $\delta$ ppm = 1.2 (t, 3H) COO$\underline{CH_2}$CH$_3$; 1.8–2.9 (m, 7H) CH, CH$_2$; 3.05 (t, 2H) —CH$_2$—S—; 3.5–3.65 (m, 2H) N—CH$_2$; 4.05 (q, 2H) CO$_2\underline{CH_2}$CH$_3$; 5.9–6.9 (ABX system, 2H) —CH=CH.

R$_f$ value: cyclohexane/acetone 2/1 = 0.53.

EXAMPLES 9b–9i

Compounds 9b–9i can be prepared from the corresponding phosphonates of the general formula VIII and 2-(1-thia-4-ethoxycarbonyl-butyl)-$\Delta^1$-pyrroline-4-aldehyde VII (n=1) by a procedure analogous to that in Example 9a.

| Example No. 9 | R = | R$_f$ values (cyclohexane/acetone 2/1) |
|---|---|---|
| (b) | [isopropyl-O-ethyl group] | 0.42 |
| (c) | [isopropyl-O-CH$_2$-phenyl group] | 0.50 |
| (d) | [ethyl-O-thienyl group] | 0.69 (cyclohexane/acetone 1/1) |
| (e) | [F-C(CH$_3$)$_2$-propyl group] | 0.55 |
| (f) | [cyclohexyl-H group] | 0.51 |
| (g) | [ethyl-thienyl group] | 0.13 |
| (h) | [ethyl-O-(chlorophenyl) group] | 0.37 |
| (i) | [gem-dimethyl pentyl group] | 0.42 |

EXAMPLE 10a 2-(1-Thia-4-ethoxycarbonyl-butyl)-4-(3-hydroxy-1-octenyl)-$\Delta^1$-pyrroline I (n=1)

10.8 ml of a 0.45 molar bis-isobornyloxy-isopropoxy-aluminate solution were added dropwise, under a stream of N$_2$, to 600 mg of 2-(1-thia-4-ethoxycarbonyl-butyl-4-(3-oxo-1-octenyl)-$\Delta^1$-pyrroline IX (Example 9a), dissolved in 10 ml of absolute toluene. The reaction had ended after 2½ hours, and the mixture was worked up by addition of about 100 ml of ethyl acetate and extraction twice with saturated sodium hydrogen tartrate solution. The sodium hydrogen tartrate phase was washed once more with ethyl acetate, the combined ethyl acetate phases were dried and concentrated and the residue was chromatographed over a Merck prepacked column, size C/silica gel (particle size: 0.063–0.2 mm) using the mobile phase cyclohexane/ethyl acetate 1/1.

Fractions 186–290 = 190 mg (3'$\beta$-epimer).

Fractions 350–490 = 220 mg (3'$\alpha$-epimer).

Yield: 0.41 g (68% of theory) of a light-colored oil. $C_{18}H_{31}NSO_3$ MW: 341.

MS: 341 (molecular mass).

NMR (CDCl$_3$): $\delta$ ppm spectra for the $\alpha$- and $\beta$-epimers are identical within the usual resolution for 60 MHz—1H. Signals as for Example 9a, and additional signals at: 3.8–4.15 (m, 1H) $\underline{CH}$—ON, and 5.45–5.55 (m, 2H) —CH=CH— (ABX system from Example 9a at 5.9–6.9 is missing).

Rf value: cyclohexane/ethyl acetate 1/1 = 0.38 (3'$\alpha$-epimer) and 0.25 (3'$\beta$-epimer).

EXAMPLES 10b–10i

Compounds 10b–10i (formula I, n=1), can be prepared from the compounds of Examples 9b–9i by reduction with bis-isobornyloxy-isopropoxy-aluminate by a procedure analogous to that in Example 10a.

| Example No. 10 | R = | NMR data (ppm) characteristic signals | MS (molecular mass) | Rf values in ethyl acetate/ cyclohexane 1/1 β/α epimer |
|---|---|---|---|---|
| b | (structure: isobutyl-O-ethyl group) | 0.9 (s, 6H) C (CH$_3$)$_2$; 1.15 (t, 3H) —OCH$_2$CH$_3$; 1.2 (t, 3H) COOCH$_3$CH$_2$; 3.3 (s, 2H) —OCH$_2$; 3.5 (q, 2H) —OCH$_2$CH$_3$; 4.05 (q, 2H) COOCH$_2$CH$_3$; 5.5–5.6 (m, 2H) olefinic protons | 371 | 0.39/0.29 |
| c | (structure: isobutyl-O-CH$_2$-phenyl) | 0.9 (d, 6H) CH$_3$; 1.2 (t, 3H) OCH$_2$CH$_3$ 3.05 (t, 2H) S—CH$_2$; 3.25 (s, 2H) —CH$_2$O—; 3.5–3.65 (m, 2H) —N—CH$_2$— 4.45 (s, 2H) CH$_2$O—C$_6$H$_5$ 5.5–5.6 (m, 2H) CH=CH; 7.2 (s, 5H) aromatic protons | 433 | 0.51/0.41 |
| d | (structure: ethyl-O-CH$_2$-thienyl) | 3.9 (d, 2H) CH$_2$O—thienyl 3.05 (t, 2H) —S—CH$_2$; 5.5–5.65 (m, 2H) olefinic protons 6.1–7.3 (triple m, 3H) thiophene | 383 | 0.25/0.19 |
| e | (structure: 2-fluoropentyl) | 3.05 (t, 2H) —S—CH$_2$; 3.5–3.65 (m, 2H) N—CH$_2$; 5.5–5.6 (m, 2H) olefinic protons | 359 | 0.34/0.24 |
| f | (structure: cyclohexyl) | 1.2 (t, 3H) COOCH$_3$CH$_3$; 1.1–2.0 (m, 3H) —CH, —CH$_2$— 3.05 (t, 2H) —S—CH$_2$— 3.55–5.6 (m, 2H) olefinic protons | 353 | 0.36/0.23 |
| g | (structure: propyl-thienyl) | 3.05 (t, 2H); 3.5–3.65 (m, 2H) N—CH$_2$; 5.5–5.6 (m, 2H) olefinic protons; 6.8–7.3 (3H) thiophene | 381 | 0.25/0.16 |
| h | (structure: ethyl-O-(3-chlorophenyl)) | 3.85 (d, 2H) CH$_2$—O—Ph, 3.05 (t, 2H) S—CH$_2$—, 5.5–5.6 (m, 2H) olefinic protons; 6.0–7.3 (m, 4H) aromatic protons | 411 | 0.33/0.18 |
| i | (structure: 2,2-dimethylpentyl) | 0.85 (s, 6H) CH$_3$; 3.05 (t, 2H) S—CH$_2$; 3.5–3.65 (m, 2H) olefinic protons | 369 | 0.42/0.28 |

EXAMPLE 11a

Sodium salt of 2-(1-thia-4-carboxy-butyl)-4-(3-hydroxy-1-octenyl)-Δ$^1$-pyrroline I (n=1, R$^1$=Na$^⊕$)

136 mg (0.4 mmole) of 2-(1-thia-4-ethoxycarbonyl-butyl)-4-(3-hydroxy-1-octenyl)-Δ$^1$-pyrroline (Example 10a) were dissolved in 30 ml of 80% strength ethanol. A solution of 67 mg of sodium in 4 ml of ethanol was added to this solution, while stirring. The mixture was stirred at 35° C. under argon for 3 hours, the solution was filtered over active charcoal and the solvent was removed from the filtrate in vacuo at 10° C. (freeze-drying). The sodium salt of the Δ$^1$-pyrroline derivative I was obtained as a colorless powder.

IR band: KBr trituration —COO$^⊖$ 1,600 cm$^{-1}$.

EXAMPLE 11b

Potassium salt of 2-(1-thia-5-carboxy-pentyl)-4-(3-hydroxy-1-octenyl)-Δ$^1$-pyrroline I (n=2, R$^1$=K$^⊕$)

134 mg of pure 2-(1-thia-5-ethoxycarbonyl-pentyl)-4-(3-hydroxy-1-octenyl)-Δ$^1$-pyrroline (Example 6), 1.1 ml of 0.5M potassium hydroxide solution and 2 ml of methanol were left to stand under an inert gas at room temperature for 24 hours. The methanol was stripped off in vacuo and the aqueous solution of the potassium salt was freeze-dried. The potassium salt of the Δ$^1$-pyrroline derivative I was obtained as a colorless powder.

IR band: KBr trituration —COO$^⊖$ 1,595 cm$^{-1}$.

EXAMPLE 11c

Triethylammonium salt of 2-(1-thia-4-carboxy-butyl)-4-(3-hydroxy-1-octenyl)-Δ$^1$-pyrroline I (n=1, R$^1$=HN$^⊕$(C$_2$H$_5$)$_3$)

An aqueous solution of 50 mg of the sodium salt from Example 11a was introduced onto a column containing 15 g of Amberlite CG-50 (triethylammonium form). The column was eluted with a 3% strength aqueous solution of triethylammonium carbonate. Freeze-drying of the eluate gave the product as a crystalline powder (decomposition 70° C.). The corresponding alkali metal or ammonium salts can be prepared from the compounds of Examples 10b to 10i by alkaline ester-hydrolysis and, where relevant, chromatography on ion exchangers, by a procedure analogous to that in Examples 11a to 11c.

EXAMPLE 12

2-(1-Thia-4-isopropoxycarbonyl-butyl)-4-(3-hydroxy-4,4-dimethyl-1-octenyl)-Δ¹-pyrroline I (n=1, R¹=CH(CH₃)₂)

369.5 mg (1 mmole) of 2-(1-thia-4-ethoxycarbonyl-butyl)-4-(3-hydroxy-4,4-dimethyl-1-octenyl)-Δ¹-pyrroline (Example 10i) were dissolved in 40 ml of absolute isopropanol, and 50 mg of pulverulent and well-dried potassium carbonate were added. The mixture was stirred for 1 hour. The solvent was stripped off in vacuo, the residue was taken up in ethyl acetate, the ethyl acetate phase was washed with water and dried and the solvent was removed in vacuo.

Yield: 345 mg of a light-colored oil. Rf value of the 3'β-epimer: cyclohexane/ethyl acetate 1/1=0.49.

Rf value of the 3'α-epimer: cyclohexane/ethyl acetate 1/1=0.34.

NMR (CDCl₃): δ ppm=4.95 (septet, 1H) C$\underline{H}$(CH₃)₂; and 1.2 (d, 6H) CH(C$\underline{H}$₃)₂.

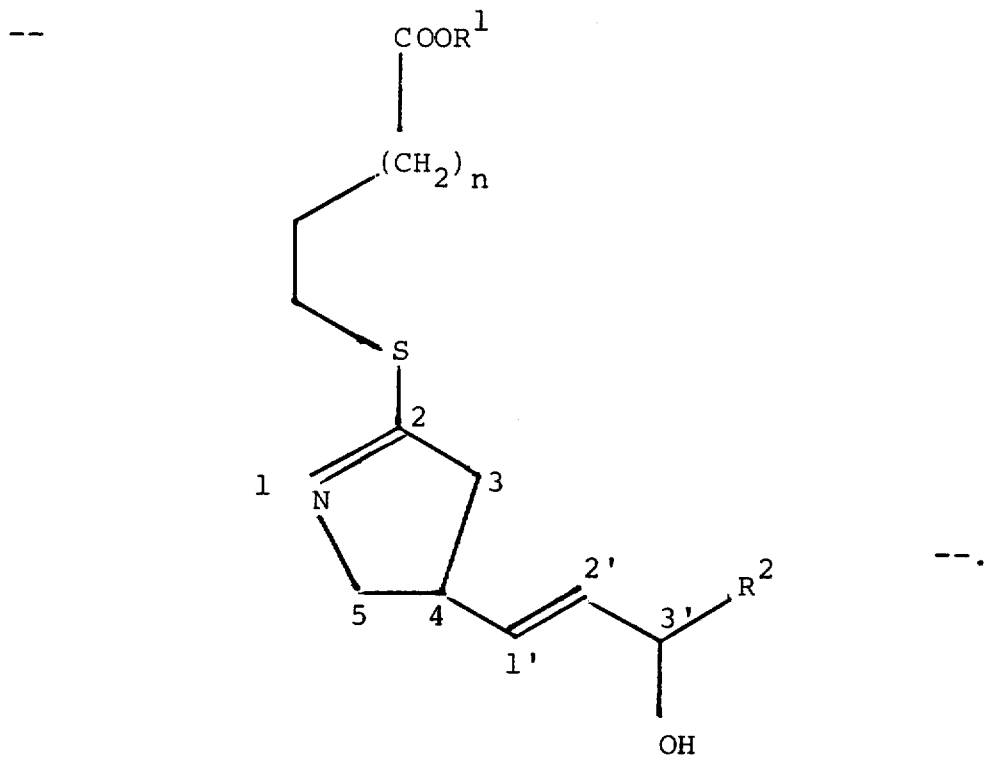

We claim:

1. A compound of the formula

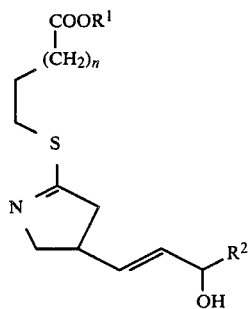

wherein
n is an integer from 0 to 4 inclusive,
R¹ is hydrogen, linear or branched alkyl having up to 8 carbon atoms, linear or branched unsaturated aliphatic hydrocarbon having 3 to 6 carbon atoms, cycloaliphatic hydrocarbon having 3 to 7 carbon atoms, araliphatic hydrocarbon having 7 to 9 carbon atoms, a physiologically acceptable metal ion, NH₄⁺, methylammonium, dicyclohexylammonium, or tris-(hydroxymethyl)-methyl ammonium, R² is phenyl or phenyl mono-substituted by halogen, trifluoromethyl and/or alkyl or alkoxy each having 1-6 carbon atoms, or is cycloaliphatic having 3-8 carbon atoms, linear or branched alkyl having up to 8 carbon atoms, linear or branched unsaturated aliphatic hydrocarbon having 3 to 8 carbon atoms, or is such aliphatic hydrocarbon substituted (a) by linear or branched alkoxy having up to 6 carbon atoms, by linear or branched alkenyloxy or alkynyloxy having 3 to 6 carbon atoms, or is such aliphatic hydrocarbon substituted (b) by halogen, cycloalkyl having 3–7 carbon atoms, phenyl, alpha- or beta-thienyl, alpha- or beta-furyl, or such thienyl or furyl mono-, di-, or tri-substituted by halogen, trifluoromethyl, and/or alkyl or alkoxy each having 1–6 carbon atoms, or is such aliphatic hydrocarbon substituted (c) by phenoxy, alpha- or beta-thienyloxy, or cycloalkoxy having 3–7 carbon atoms, or by such phenoxy, thienyloxy, or cycloalkoxy which is mono-, di-, or tri-substituted by halogen, trifluoromethyl, and/or alkoxy having 1–6 carbon atoms.

2. A compound as in claim 1 which is 2(1-thia-4-ethoxycarboxyl-butyl)-4-[3-hydroxy-5-(2-thienyl)-1-pentenyl]-delta-1-pyrroline.

3. A hypotensive composition comprising a hypotensively effective amount of a compound as in claim 1 together with a physiologically acceptable carrier therefor.

4. A method for treating hypertension in a patient suffering therefrom, which comprises administering to said patient a hypotensively effective amount of a compound as in claim 1.

* * * * *

UNITED STATES PATENT AND TRADEMARK OFFICE
CERTIFICATE OF CORRECTION

PATENT NO. : 4,548,936

DATED : October 22, 1985

INVENTOR(S) : Gerhard Beck et al.

It is certified that error appears in the above-identified patent and that said Letters Patent is hereby corrected as shown below:

In the Abstract, replace the formula by the following on the attached sheet.

Signed and Sealed this

Eleventh Day of March 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,548,936  Page 2 of 2
DATED : October 22, 1985
INVENTOR(S) : Gerhard Beck et al.

It is certified that error appears in the above-identified patent and that said Letters Patent is hereby corrected as shown below: